United States Patent Office

Plant Pat. 3,342
Patented May 22, 1973

3,342
PEACH TREE

Wilfred A. Pratt, Wenatchee, Wash. 98801

Filed June 28, 1971, Ser. No. 157,697
Int. Cl. A01h 5/03
U.S. Cl. Plt.—43 1 Claim

ABSTRACT OF THE DISCLOSURE

A mutant of the Red Haven peach tree, with fruit similar in appearance and time of ripening to Early Red Haven (Plant Patent 2,343) but characterized in the greater firmness and longer storage life of its fruit than that of Early Red Haven.

DESCRIPTION

This discovery relates to a new and distinct variety of peach tree which originated as a sport or mutation limb found growing on a Red Haven peach tree in the applicant's orchard at 1609 Maple Street, Wenatchee, Wash., U.S.A. This new mutation variety has been asexually reproduced both at the above identified orchard and at Sun Crest Orchard located near Columbia Siding in Douglas County, Wash., U.S.A., through three successive generations and in each instance has exhibited all of the characteristics of the original sport limb and is thereby established as stable.

*Tree*

The tree, including the vegetative growth thereof, is similar to the parent Red Haven peach tree, the growth rate being medium to vigorous.

*Fruit*

The fruit of this new variety is medium to large, appearing similar to and maturing at the same time as the fruit of adjacent Early Red Haven trees (Plant Patent 2,343). As with its parent, Red Haven, the fruit is freestone when fully tree-ripened and the meat is firm and smooth with very little fiber. The pit area of the new variety is free of red color found around the pit area of Red Haven.

However, as the characterizing feature of the new variety, its fruit is materially firmer than that of Early Red Haven. After 20 days in storage at approximately 34 degrees Early Red Haven showed bruised areas. The new variety did not show these areas even though the fruit was handled in the same manner. It is also found to be capable of much longer storage life. Stored fruit of Early Red Haven and of the new variety in equally ripened condition, handled and stored in the same manner, showed that the new variety has an effective commercially acceptable maximum storage life of about 45 to 50 days whereas the fruit of Early Red Haven (also of Red Haven) is only about 35 days. The flesh of the new variety is resistant to browning after processing, making it distinctively different from its parent Red Haven which turns brown rapidly when processed and removed from the container.

I claim:

1. The new and distinct variety of peach tree characterized by the greater firmness and longer storage life of its fruit from that of the nearest similar or related variety Early Red Haven (Plant Patent 2,343).

No references cited.

ROBERT E. BAGWILL, Primary Examiner